(12) United States Patent
Wolff

(10) Patent No.: US 9,579,439 B2
(45) Date of Patent: Feb. 28, 2017

(54) METHOD AND DEVICE FOR DETERMINING A RECIRCULATION STATE

(71) Applicant: B. BRAUN AVITUM AG, Melsungen (DE)

(72) Inventor: Henrik Wolff, Witzenhausen (DE)

(73) Assignee: B. BRAUN AVITUM AG, Melsungen (DE)

( * ) Notice: Subject to any disclaimer, the term of this patent is extended or adjusted under 35 U.S.C. 154(b) by 510 days.

(21) Appl. No.: 14/221,927

(22) Filed: Mar. 21, 2014

(65) Prior Publication Data

US 2014/0291244 A1 Oct. 2, 2014

(30) Foreign Application Priority Data

Mar. 28, 2013 (DE) .................. 10 2013 103 220

(51) Int. Cl.
*A61M 1/16* (2006.01)
*A61M 1/36* (2006.01)

(52) U.S. Cl.
CPC ........ *A61M 1/1605* (2014.02); *A61M 1/1615* (2014.02); *A61M 1/3658* (2014.02)

(58) Field of Classification Search
CPC . A61M 1/1605; A61M 1/1615; A61M 1/3658
See application file for complete search history.

(56) References Cited

U.S. PATENT DOCUMENTS

| | | | |
|---|---|---|---|
| 5,100,554 | A | 3/1992 | Polaschegg et al. |
| 5,507,723 | A | 4/1996 | Keshaviah |
| 5,588,959 | A | 12/1996 | Ahmad et al. |
| 5,685,989 | A | 11/1997 | Krivitski et al. |
| 6,156,002 | A | 12/2000 | Polaschegg et al. |

(Continued)

FOREIGN PATENT DOCUMENTS

| | | |
|---|---|---|
| DE | 39 38 662 | 7/1991 |
| DE | 197 39 100 | 2/1999 |

(Continued)

OTHER PUBLICATIONS

German Search Report for DE 10 2013 103 220.6 dated Dec. 3, 2013.

(Continued)

*Primary Examiner* — John Kim
(74) *Attorney, Agent, or Firm* — RatnerPrestia

(57) ABSTRACT

A method and a device for determining a recirculation during a dialysis on the basis of the response of the dialysis system to an alteration of a system-related operating value are described. Recirculation may be determined by establishing, at the side of the dialysis liquid, a reference parameter that represents the concentration of uremic toxins from the extracorporeal circulation, and calculating a target parameter for a system-related target operational value from the reference parameter, presetting the system-related target operational value and establishing an actual parameter related to the system-related target operational value, determining an actual comparative value from the actual parameter and the reference parameter related to the system-related target operational value and comparing the actual comparative value with a system-specific target comparative value related to the system-related target operational value, and converting the comparison result into a recirculation degree.

9 Claims, 4 Drawing Sheets

(56) References Cited

U.S. PATENT DOCUMENTS

| | | |
|---|---|---|
| 6,582,656 B1 | 6/2003 | Steuer et al. |
| 6,702,774 B1 | 3/2004 | Polaschegg |
| 7,097,630 B2 | 8/2006 | Gotch et al. |
| 7,674,236 B2 | 3/2010 | Daniel et al. |
| 7,815,852 B2 | 10/2010 | Sternby |
| 8,747,663 B2 | 6/2014 | Kopperschmidt |
| 8,858,486 B2 | 10/2014 | Zhang et al. |
| 2002/0009385 A1 | 1/2002 | Krivitski et al. |
| 2002/0062098 A1 | 5/2002 | Cavicchioli et al. |
| 2004/0073153 A1 | 4/2004 | Bosetto et al. |
| 2005/0133449 A1 | 6/2005 | Sternby |
| 2005/0148923 A1 | 7/2005 | Sternby |
| 2007/0112289 A1 | 5/2007 | Cavalcanti et al. |
| 2007/0131595 A1 | 6/2007 | Jansson et al. |
| 2008/0149563 A1 | 6/2008 | Ash |
| 2009/0054822 A1 | 2/2009 | Murakami et al. |
| 2012/0217189 A1 | 8/2012 | Ahrens et al. |
| 2012/0298581 A1 | 11/2012 | Wehmeyer et al. |
| 2013/0226065 A1 | 8/2013 | Wolff et al. |

FOREIGN PATENT DOCUMENTS

| | | |
|---|---|---|
| DE | 197 47 360 | 4/1999 |
| DE | 695 31 137 | 4/2004 |
| DE | 10 2004 023 080 | 12/2005 |
| DE | 10 2005 001 051 | 7/2006 |
| DE | 10 2007 056 475 | 6/2009 |
| DE | 10 2010 015664 | 10/2011 |
| DE | 10 2011 102 962 | 11/2012 |
| EP | 0 900 094 | 3/1999 |
| EP | 1 083 948 | 3/2001 |
| EP | 1 604 698 | 12/2005 |
| WO | WO 95/32010 | 11/1995 |
| WO | WO 98/32477 | 7/1998 |
| WO | WO 99/62574 | 12/1999 |
| WO | WO 00/24440 | 5/2000 |
| WO | WO 2011/026647 | 3/2011 |
| WO | WO 2012/062257 | 5/2012 |

OTHER PUBLICATIONS

European Extended Search Report for EP 14158083.7 dated Jul. 10, 2014.

Walter K. Hörl and Christoph Wanner (Hrsg.), Dialyseverfahren in Klinik and Praxis, 6. Aufl., Suttgart 2004, ISBN 3-13-497706-0, S. 209.pdf.

Walter K. Hörl and Christoph Wanner (Hrsg.), Dialyseverfahren in Klinik and Praxis, 6. Aufl., Suttgart 2004, ISBN 3-13-497706-0, S. 209.pdf, with translation.

Uhlin, Fredrik, "Haemodialysis Treatment Monitored On-Line by Ultra Violet Absorbance," Linkoeping Univ., 2006.

METHOD AND DEVICE FOR DETERMINING A RECIRCULATION STATE

CROSS REFERENCE TO RELATED APPLICATIONS

This application claims priority to German application DE 10 2013 103 220.6 filed Mar. 28, 2013, the contents of such application being incorporated by reference herein.

FIELD OF THE INVENTION

The present invention relates to a method and a device for determining or measuring (detecting) a recirculation at the side of the dialysis apparatus within a patient-side inlet/outlet element (patient access), preferably of a shunt.

BACKGROUND OF THE INVENTION

The dialysis is an extracorporeal blood purification method which is used as a substitution method in case of renal failure. Apart from a kidney transplant, dialysis is one of the most efficient and thus most important renal substitution therapies in case of chronic renal failure and one of the treatment options for acute renal failure. The term "dialysis" or, in general, "blood purification" of this kind is to be understood as an exchange of substances through a membrane, with blood/plasma being present on the one membrane side and a dialysis liquid being present on the other side of the membrane or flowing along it.

During a treatment, blood is pumped out of the patient via a patient access (shunt), is conveyed past a dialysis membrane in the dialyzer (filter) and returned to the patient in cleaned condition. Any poisonous substances (metabolic degradation products) and uremic toxins consisting of small and medium-sized molecular substances (which are able to penetrate the membrane) are transported in a hemodialysis or hemofiltration or hemodiafiltration operating mode (treatment mode) of the dialysis apparatus from the blood mainly by diffusion and/or convection via the membrane to the other filter side into the dialysis liquid solution and are removed in this way. With the exception of the hemofiltration, there is a constant flow of fresh dialysis liquid through the dialyzer (preferably approximately 500 to 800 ml/min), with the preferred flow direction of the dialysis liquid in the dialyzer being countercurrent to the blood flow.

Usually, a hemodialysis treatment is carried out for approximately 4 to 5 hours (dialysis overnight up to 8 hours) for every treatment and at least three times a week (depending on the body weight, renal residual function, cardiac output). Patients who perform the hemodialysis at home avoid the problematic, longer treatment interval at the weekend and carry out the dialysis more frequently, as a rule every second day or even daily.

An important factor of influence on the quality of the dialysis is the blood flow. Generally speaking, the higher the blood flow, the better the result of the treatment. However, it may happen that problems occur in the dialysis shunt implanted in the patient for taking blood and returning the cleaned blood (e.g. restricted or insufficient flow due to wrong/imperfect positioning in the patient, damage etc.), in particular if the blood flow is high in the extracorporeal system. The specific level of the blood flow at which these problems will occur depends on the quality of the patient access and on the blood flow through the shunt as well as its integrity (no stenosis or aneurysm).

The problem/phenomenon of a so-called "recirculation" in the shunt may occur both with a low flow of blood through the shunt and in the state in which the shunt flow is still significantly higher than the preset blood flow. This means that already cleaned blood from the venous needle applied to the patient is sucked in by the arterial needle likewise applied to the patient and mixed with the blood still to be cleaned. This reduces the cleaning performance and the treatment results are perhaps not satisfactory. The same may happen if the arterial and venous needles are swapped by mistake when connecting the patient to the dialysis apparatus. In this case, the venous needle is upstream of the arterial needle and a recirculation effect occurs, too. Similarly, with low shunt quality fluidic effects result in recirculation.

DESCRIPTION OF THE RELATED ART

Currently, measuring the recirculation is carried out with complex methods which are based e.g. on the administration of a bolus (for example NaCl or temperature or conductivity).

A basic objective of the majority of these methods (like that of the present invention) is to establish a system which is capable of determining the recirculation via a measurement which is internal to the machine and is as simple as possible, in particular at the beginning of a treatment.

The determination of a recirculation in the shunt of the patient is already presented in prior art by various methods. In dialysis apparatus which are known per se, the identification of the recirculation is realized for instance by a temperature check (EP 0 900 094). To this end, the blood conducted outside the body is provided in the venous line portion with a bolus in the form of a temperature pulse. The measurement of the temperature in the arterial line portion allows conclusions to be drawn as to the percentage of the recirculation.

Further, the respective prior art offers a measurement in the nature of an offline dialysis, performed on the basis of a measurement of the conductivity and likewise operating with the administration of a suitable bolus. Here, the recirculation in the shunt of a dialysis patient is determined by measuring the conductivity. With this method, too, an electrolyte bolus is administered to the venous hose portion and modifies the conductivity of the liquid. Due to the determination of the conductivity in the arterial hose portion, conclusions can be drawn as to the level of the recirculation (U.S. Pat. No. 7,815,852).

Moreover, a recirculation may basically also be determined with a hematocrit sensor. In doing so, the hematocrit of the blood is changed by administering a defined bolus to the venous line portion. The determination of the hematocrit in the arterial line system allows for the detection of recirculation. Technical proposals which are based on this principle are disclosed, for instance, in U.S. Pat. No. 5,685,989. These known products are based either on the measurement of the recirculation with electromagnetic radiation in the visible range or on the measurement of the recirculation by ultrasound.

Problems of the Prior Art

The described methods/products are able to determine the recirculation in the patient access in various ways. However, all the above-mentioned methods require the administration of a bolus to the venous or arterial portion of the extracorporeal line system, with the bolus being subsequently measured in the arterial portion.

Further, the administered bolus has to have defined properties which significantly differ from those of the extracorporeal blood, so that it can be detected without any doubt by measurement technology. In addition, one or more additional detectors/sensors are required depending on the method in order to be able to evaluate the bolus in a quantitative and qualitative manner. The particular difficulty with these methods, however, is the fact that the extracorporeal line systems are very different in terms of their quality and nature, which cannot be taken into consideration during the measuring methods. This circumstance might cause a falsification of measuring results.

SUMMARY OF THE INVENTION

It is an object of at least one aspect of the invention to provide a control method and a device for determining the recirculation in the shunt, which can do without any addition of a bolus and thus do neither affect the blood side nor the side of the dialysis liquid by a bolus (disturbance).

One aim is that no further (measuring) apparatus are needed on the blood side for carrying out a recirculation measuring process according to aspects of the invention, as only machine-related parameters shall be varied by control engineering to allow a measurement (preferably in the on-line mode). In addition, the measurement shall take place exclusively on the side of the dialysis liquid of the apparatus and hence without any additional technical effort on the blood side.

An object of the present invention is to adjustor to change the blood flow starting from a reference value (e.g. a blood flow of 50 ml/min) at which there exists (knowingly and demonstrably) the state of completed purification (and with no recirculation or negligible recirculation) to a desired individual treatment value (e.g. a target blood flow of 300 ml/min at an average). During this adjusting/changing process, the system response, i.e. the reaction of the system with regard to a currently measurable actual parameter (directly or indirectly represented by the concentration of uremic toxins in the desired treatment operational mode of for example 300 ml/min), triggered by the change in the blood flow, is established with the aid of a sensor and correlated—with a computer-assisted comparator—to a target parameter which has been calculated from a previously measured reference parameter. In this way, an actual comparative value is calculated from the measured actual parameter and the calculated target parameter, which finally is compared with a system-specific target comparative value which has been established and stored beforehand; from these values, a difference value can be established. Said difference value correlates to a related recirculation degree for the preset blood flow (desired treatment operational mode).

This recirculation degree is characterized in that already cleaned blood is supplied to and discharged from the extracorporeal circulation via at least one blood inlet/outlet element (which may also be represented by two structurally/spatially separated elements) independently of its constructional design and/or arrangement on/in the patient's body, whereby the extracorporeal contamination level changing with respect to the intracorporeal contamination level. Here, the recirculation may be caused by:
- the construction/arrangement of the at least one inlet/outlet element (also known as shunt recirculation) or
- the circulation through the cardiopulmonary system (also known as cardiopulmonary recirculation).

Here, it is referred to the fact that the term "without recirculation/missing recirculation" is to be understood as a state in which there prevails a recirculation between 0 and a negligible value. By way of example, recirculation may occur with swapped arterial and venous needles also with a reference blood flow of 50 ml/min. This, however, would be negligibly small (50/4000) for typical cardiac volume outputs of for example 4000 ml/min and would have no impact on the method according to aspects of the invention. Moreover, the term "completed purification" is to be understood as the following state: a completed purification with respect to a substance from the blood of the patient exists by definition if the concentration of the respective substance in the venous (returning) hose segment is "zero".

For simplification purposes, the term "contamination of the dialysis liquid" will also be used in the following for the used dialysis liquid draining off the dialyzer.

The procedure which is explained above will be applied in case the blood purification system is operated for example in a hemodialysis mode, i.e. in an operational mode in which a fresh dialysis liquid is conveyed through a dialyzer with a predetermined volume flow>0. As an alternative and according to another basic idea of the present invention, it is also possible to operate the system in a filtration mode (pure convection) in which no new/fresh dialysis liquid is supplied to the dialyzer, i.e. the mass transport takes place from the blood side of the dialyzer via the membrane into the dialysis liquid chamber; in this case, too, there is no recirculation for example for a blood flow of 50 ml/min as a reference value. It is no longer required that the reference parameter established in this process has to be extrapolated to a (theoretical) target parameter for the intended operational mode of the treatment (e.g. 300 ml/min) (i.e. a determination of the clearance is not required), but can be directly correlated for this particular ultrafiltration mode to a currently measurable actual parameter in the desired operational mode of the treatment (e.g. 300 ml/min).

Specifically stated, (only) one sensor is basically used for determining an optical absorbance/absorption (reference parameter and actual parameter) on the side of the dialysis liquid (i.e. not on the blood side) of a blood purification apparatus, said sensor preferably operating with electromagnetic radiation in the UV range. Here, it is explicitly pointed out that any other online measuring methods of known type can be employed, too. Such a UV measuring method of the preferred type is described for example in the paper of Fridolin et al. (Uhlin F., Haemodialysis treatment monitored online by ultraviolet absorbance, University of Linköping, Medical Dissertations no. 962, Department of Medicine and Care Division of Nursing Science & Department of Biomedical Engineering, 2006), and a corresponding sensor is described in the patent document EP 1 083 948, so that reference can be made here to this generally known prior art pertaining to the specialized knowledge.

A concrete basis for the measuring method according to aspects of the invention in a first preferred case of a hemodialysis mode (HD mode) as an operational mode is that a completed purification is achieved with a known blood flow of 50 ml/min (i.e. a previously known reference blood flow for determining the reference value) in the preferred exemplary embodiment in the absence of a recirculation (for example complete removal of uremic toxins from the blood in the case of a UV measuring method). In this case, it is readily possible to calculate the actual clearance as a preferred actual comparative value (proportion of the blood flow relative to the total blood flow, which is completely free from any uremic toxins) for any current (treatment) blood flow, according to aspects of the invention starting from an absorbance value as a preferred measured/measurable actual parameter for the respective/current (treatment) blood flow taking into account a previously measured reference absorbance value (preferred reference parameter). Finally, the recirculation degree for the intended treatment blood flow can be deduced on the basis of the determination of the clearance. To this end, the following control technology method steps can be carried out in sequence:

a. determining/measuring a reference parameter, for instance the (reference) absorbance value A(50) in the used dialysis liquid (draining off the dialyzer) for a reference blood flow of preferably 50 ml/min (under the prerequisite of a completed purification and missing recirculation), b. determining/measuring an actual parameter, for instance the actual absorbance value in the used dialysis liquid for the selected/desired (target) treatment flow A(BBF) (preferably at 300 ml/min) as a system reaction, c. starting from the reference parameter, preferably the (reference) absorbance value A(50) at 50 ml/min, a target parameter, preferably the theoretical (target) value A(BBF,theo) of the absorbance with an assumed (theoretical) completed purification and (theoretical) absence of recirculation of the selected treatment flow A(BBF) (preferably 300 ml/min) can be calculated as follows: A(50)*(BBFml/min/50 ml/min)=A(BBF,theo)

d. starting from the ratio between the measured actual parameter, preferably the actual absorbance value A(BBF) (with an actually existing, possibly incomplete purification) and the theoretically calculated/extrapolated target parameter, preferably the target absorbance value A(BBF, theo) (for theoretical completed purification), an actual comparative value, preferably the current clearance K(BBF, actual) (specified in ml/min) can be determined by multiplying this ratio with the blood flow BBF, i.e.: K=[A(BBF)/A(BBF,theo)]*BBF e. subsequently, the established actual comparative value, preferably the current clearance K(BBF, actual) can be compared with a predetermined (filter-specific) and deposited target comparative value, for example a target clearance K(BBF, theo) for this filter in case of missing recirculation. This value is individually established for each filter and, for example, is stored in a memory unit or input by hand.

Finally, the recirculation Rec can be calculated or determined/defined from the deviation established by the comparison according to method step e, preferably a clearance deviation ΔK (i.e. $(K_{theo}-K_{ist})$).

As an alternative to this and as a basis for the measuring method according to the aspects of the invention, the system can be run according to a second preferred case in an ultrafiltration mode (pure filtration) as an operational mode. Here again, a reference parameter is measured at a reference blood flow for which there is knowingly no recirculation, for example at a blood flow of 50 ml/min. As a transfer of harmful substances from the blood into a dialysis liquid occurs here exclusively by convection (dialysis liquid volume flow=0) in the dialyzer, a determination of the clearance is not necessary in this case. This means that the reference parameter is now directly correlated to the actual parameter for the desired treatment blood flow (e.g. 300 ml/min), from which the recirculation in the desired treatment operational mode can be deduced. For this purpose, the following method steps can be carried out in succession:

a. determining/measuring a reference parameter, for instance the (reference) absorption/absorbance with a reference blood flow of preferably 50 ml/min (under the prerequisite of missing recirculation), b. determining/measuring an actual parameter, for instance the actual absorption/actual absorbance with the selected/desired (target) treatment flow BBF (preferably at 300 ml/min) as a system reaction, c. starting from the measured reference parameter, preferably the (reference) absorption at 50 ml/min, a further parameter can be determined, for example the reference absorbance A(50) which can be equated to a target parameter, preferably the theoretical (target) value A(BBF,theo) of the absorbance for an assumed (theoretical) absence of recirculation at the selected treatment flow BBF (preferably 300 ml/min) as an identical value: A(50)=A(BBF, theo)

d. starting from the ratio between the measured actual parameter, preferably the actual absorbance value A(BBF) (with an actually existing, possibly incomplete purification) and the target parameter, preferably the target absorbance value A(BBF, theo) (with theoretical completed purification without recirculation), which corresponds in this case to the reference value A(50), the recirculation Rec can be immediately established from:

Rec(in %)=(1−(A(BBF)/A(50))*100 or

Rec(in ml/min)=(1−(A(BBF)/A(50))*BF

These two alternative control methods which follow the same procedural principle and are only adapted to different modes of operation, i.e. the hemodialysis mode and the hemofiltration mode, are illustrated in comparison in the enclosed FIG. 4. This procedural principle or control frame which can be taken from FIG. 4 can be described, being aware of the two above alternative concepts of the invention, as follows:

determining a reference value, which can be derived from the contamination of the dialysis liquid, for a system-related operational state (for instance a blood flow of 50 ml/min) for which—as is known—there is no shunt recirculation, ramping up the system to a desired system-related (target) operational state (for instance a blood flow of 300 ml/min) and determining a current/real value, which can be derived from the contamination of the dialysis liquid, for this system-related operational state, for which a shunt recirculation is assumed, determining an ideal value, which can be derived from the contamination of the dialysis liquid, for this system-related operational state for which there is no recirculation in the ideal case, and defining the true shunt recirculation for this system-related operational state directly or indirectly from the current value and the ideal value.

Moreover, in particular in the enclosed FIG. 1, a straight line is to be seen which arises if different recirculation degrees are produced and the impact on the cleaning performance of the currently used filter (dialyzer) is measured/determined according to the preceding method steps. It is to be seen that the gradient b of this straight line is quasi (−1) (i.e. negative) which means that the change in the clearance can be directly converted into a recirculation Rec.

This consideration results in the calculation of the shunt recirculation according to Rec=K(target)−K(measured) [in ml/min]

with

Rec representing the recirculation,

K(measured) representing the clearance value determined for the currently set blood flow and K(target) represents the stored value for the special filter (dialyzer) according to the preset blood flow as well as for an assumed completed purification.

If the gradient of the straight line (factor b) is not equal to 1 or (−1) (in case of a negative gradient), it is to be taken into consideration as a factor in the process of converting the clearance deviation ΔK into the recirculation value Rec. In this case, the result is:

$$Rec(\%)=[K(target)-K(measured)]/(factor\ b)\ [in\ \%]$$

It is also possible to use sequential phases (pure ultrafiltration—also referred to as UF) for the conversion. The calculation is carried out here just as described above, but there is no longer a need to know the filter, because uremic toxins in their blood plasma concentration are washed in the UF mode to the side of the dialysis liquid by pure convection. In other words, as the screening coefficient of the fiber membrane of a dialyzer is generally known for small molecular substances, there is no need to specifically know the filter with this mode. (Here, "screening coefficient" is defined as follows: A liquid is caused to flow over the dialyzer membrane, without having any passage of the dialysis liquid, and then the ratio is determined from the concentrations of a marker substance in the filtrate in relation to the input fluid).

In the UF mode, it is hence sufficient to correlate a measured value of the absorbance at the selected (desired) treatment blood flow of preferably 300 ml/min to the measured value of the absorbance without shunt recirculation (reference reading at preferably 50 ml/min), as already explained above. Then, one has the above-mentioned formula:

$$Rec(\%)=(1-(A(300)/A(50))*100 \qquad [general\ formula]$$

An extrapolation of the (reference) absorbance value at a blood flow of 50 ml/min to the treatment blood flow (preferably 300 ml/min) is not required, because it is not the blood flow which is crucial, but only the preset transmembrane (convective) flow.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 2:
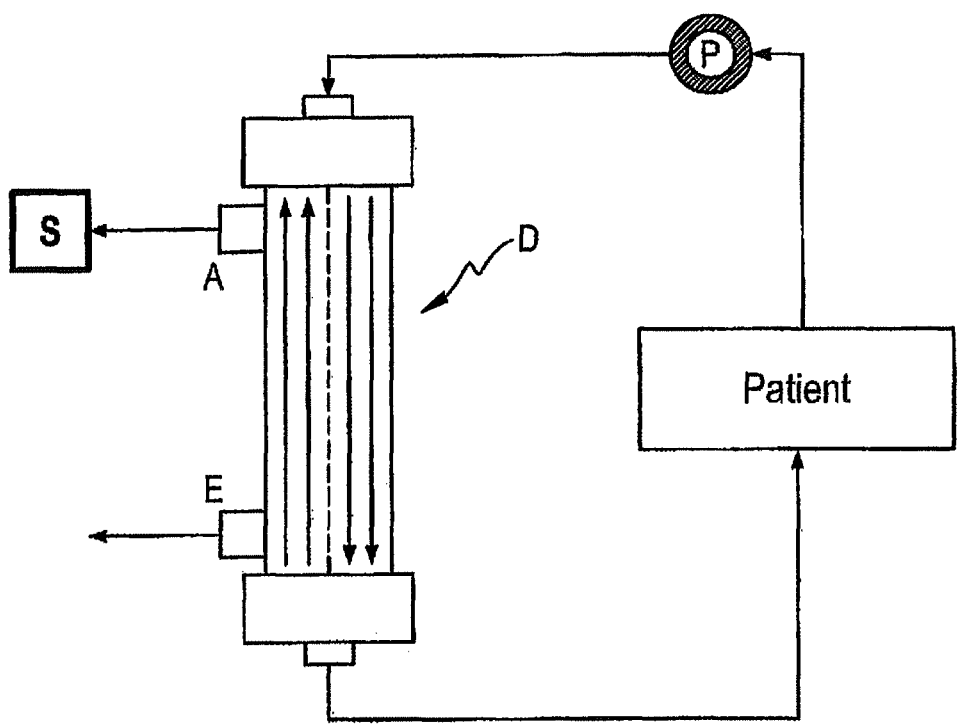
FIG. 2 shows the basic structure of a dialyzer comprising a measuring device according to aspects of the invention at the dialyzer outlet.

FIG. 2 illustrates the way in which blood is circulated via the pump P through a dialyzer D of a predetermined type and subsequently supplied back to the patient.

Figure 1:
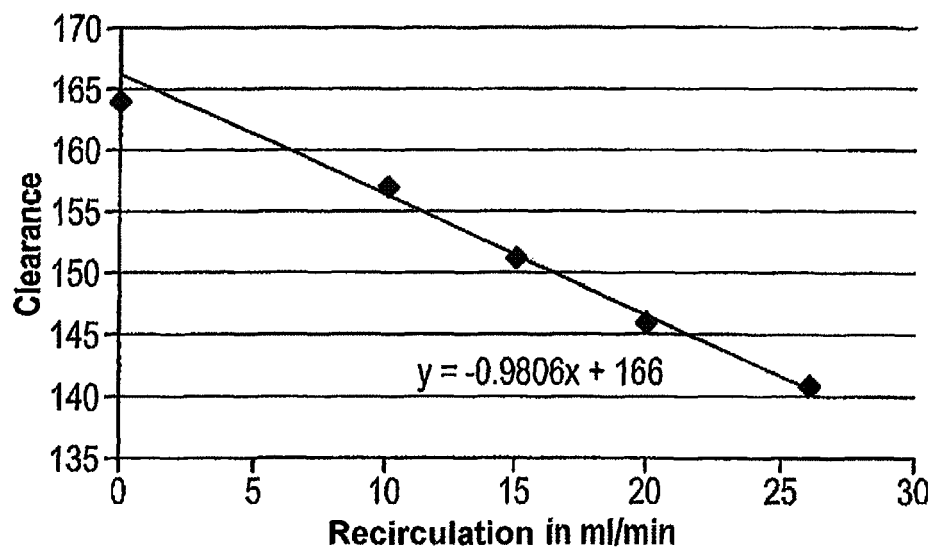
FIG. 1 shows an example of a clearance recirculation diagram (for converting a clearance value into a recirculation value) for a dialyzer of a specific type.

Within the dialyzer D, a purification solution (dialysis liquid) is fed into a dialyzer inlet E preferably according to the countercurrent principle and subsequently washed around the hollow fibers of the dialyzer D having a known construction. As is known, uremic substances are removed from the blood circulation in this way and removed with the purification solution (dialysis liquid). The drain A for the (used) purification solution is provided with a sensor (UV measuring equipment) S generating a signal (according to the principle of UV spectrometry) which is fed to a computer (not shown in further detail) and correlates to a concentration quantity (absorbance value) with regard to removed substances (uremic toxins). The correlating concentration quantity will then be compared by the computer or a comparator of the computer with a theoretical concentration quantity for this specific dialyzer under theoretically assumed, optimum conditions (without recirculation), whereupon conclusions are drawn to a related recirculation degree on the basis of a detected deviation and for example by use of a diagram according to FIG. 1.

Figure 4:
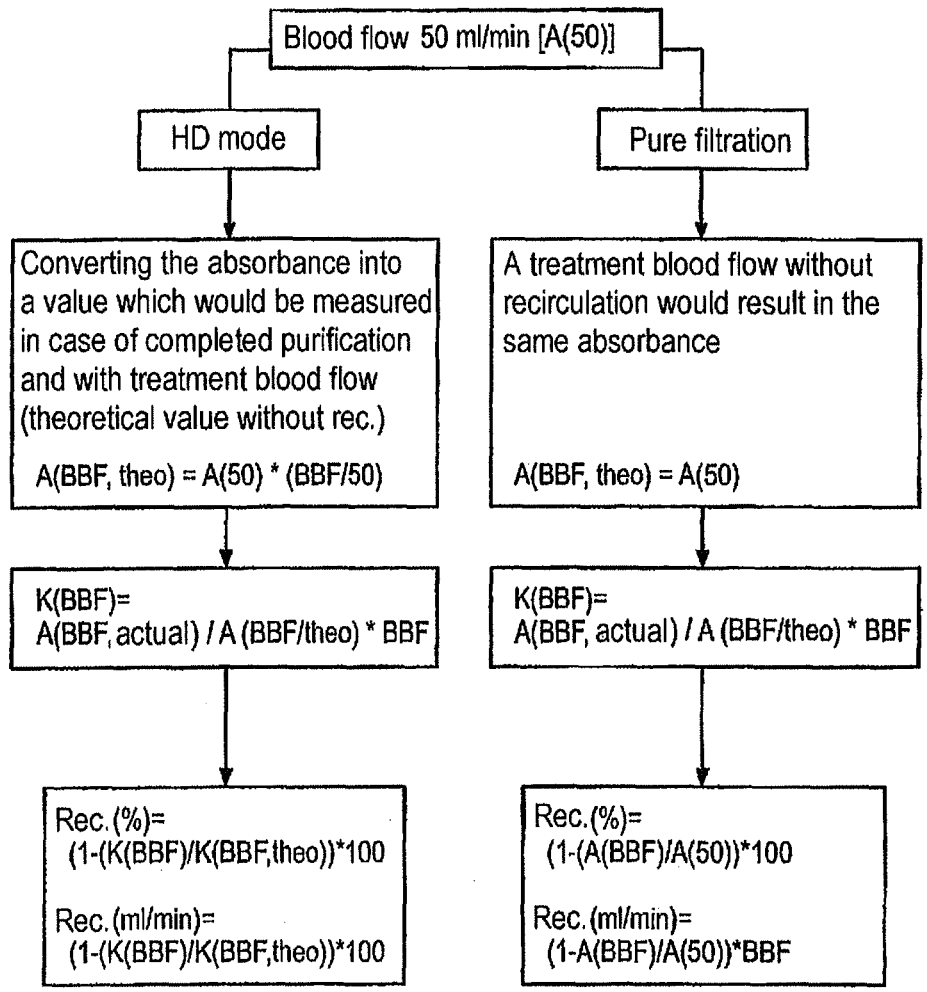

Therefore, said device can be specifically described by way of example for the case of a hemodialysis according to FIG. 4 as follows:

a. at the beginning of a treatment, a blood flow of 50 ml/min (completed purification and absence of recirculation) is run for approximately 2 min. and the reference absorbance of the effluent purification solution is determined, for example A(50)=0,458;

b. then, the blood flow is ramped up to the treatment flow BF=300 ml/min and the actual absorbance is determined again, for example A(300)=1,383;

c. subsequently, the target value which is to be expected by theory for the absorbance A(300,theo) is established on the assumption of a completed purification without recirculation, for example A(300,theo)=2,748;

d. finally, the clearance is calculated with the ratio between the measured actual absorbance A(300) and the theoretically expected target absorbance assuming a completed purification without recirculation A(300,theo). K=[A (300)/A(300,theo)]*300 ml/min=151 ml/min;

e. as a last point, the recirculation is determined with the correlation established for this filter, for example from $$Rec(ml/min)=[K(target)-K(measured)]/b=(166-151)\ ml/min/1=15\ ml/min.$$

Thus, the recirculation for this example is 15 ml/min of the blood flow. The unit, especially in this example, is ml/min (blood flow). The unit of the recirculation may basically also be indicated in another way—for example in %.

Having determined the recirculation in the shunt, it is further possible to determine the theoretical shunt flow, if the recirculation is not equal to, i.e. larger than 0%. For this purpose, calculation formulas according to Mercadel are available which can be applied in this case. In particular, the following is true:

$$Qa=(Qb-UF)+(1-R)/R$$

where
Qa: theoretical shunt flow
Qb: blood flow
UF: ultrafiltration value
R: recirculation degree If the above-mentioned determination of the shunt flow is not possible in this way, for instance because the recirculation is 0%, the blood system may be operated, so to speak, in the inverse operation by swapping the venous and arterial accesses at the shunt. To this end, the prior art already includes various mechanical devices for simplifying such a process of switching from normal operation to the inverse operation.

Figure 3:
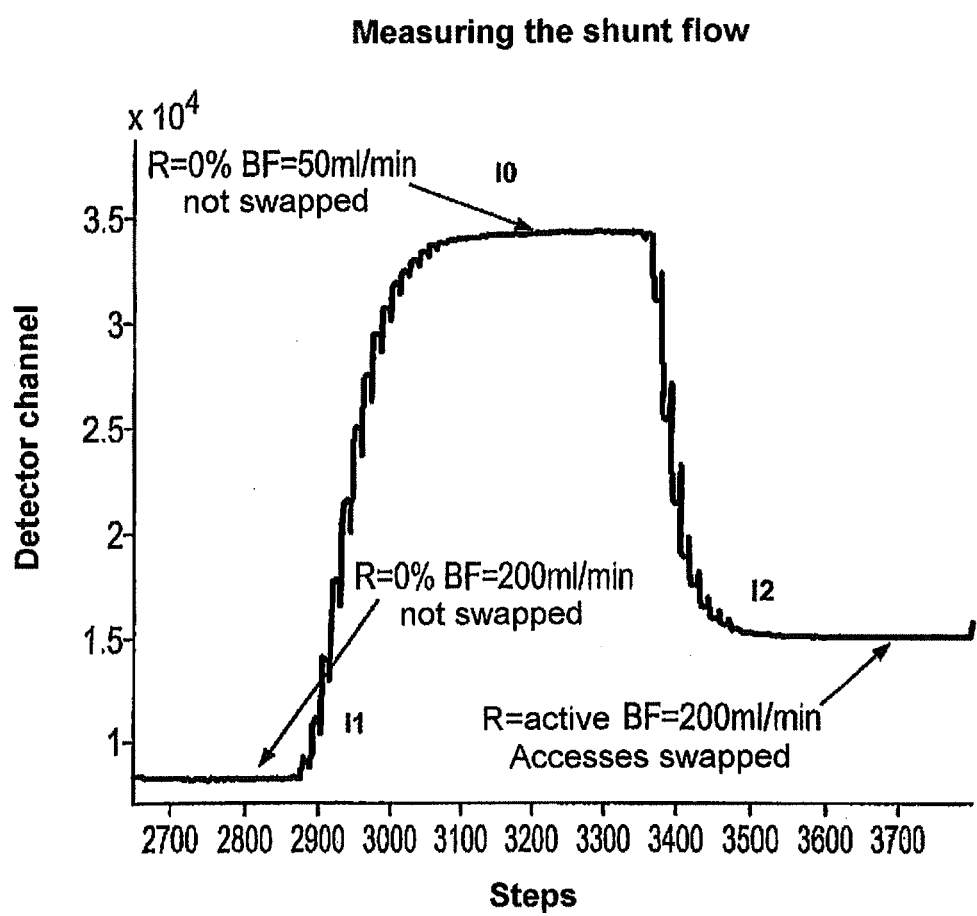
FIG. 3 shows a curve relating to the intensity I (of a UV measuring signal) for different operational states of the system and FIG. 4 shows a comparison of the basic steps of the control method according to aspects of the invention of a blood purification system in the hemofiltration mode and in the ultrafiltration mode.

If the system will then be operated in the inverse mode, a recirculation occurs which is enforced by this measure. This allows for the determination of the theoretical shunt flow by determining the clearance for both cases according to the above description with the formula of Mercadel. Here, the following is true:

$$Qa=(K1*K2)/(K1-K2)$$

wherein
K1: clearance in the normal operation
K2: clearance in the inverse operation after switching FIG. 3 shows a diagram illustrating the intensity for a treatment blood flow of 200 ml/min with a recirculation of 0%, a subsequent reduction of the blood flow to 50 ml/min with a recirculation of still 0% and a final process of switching to the inverse operation with a simultaneous increase of the blood flow to 200 ml/min again.

The clearances K1 and K2 prior to and after the switching process can be calculated from the graphically illustrated intensity values I1, I0 and I2 for the above blood flow parameters: 200 ml/min (normal operation), 50 ml/min (normal operation), 200 ml/min (inverse operation). Here, the following applies:

$$K1=I1*Qb1/I0 \text{ and}$$

$$K2=I2*Qb2/I0$$

where
Qb1: blood flow prior to switching (for example 200 ml/min in the present case)
Qb2: blood flow after switching (for example 200 ml/min in the present case)

In summary, the present invention relates to a method and a device for determining a recirculation during a dialysis on the basis of the response of the dialysis system to an alteration of a system-related operating value, comprising the following basic method steps:

determining a reference value, which can be derived from the contamination of the dialysis liquid, for a system-related operational state (for instance a blood flow of 50 ml/min) for which—as is known—there is no shunt recirculation, ramping up the system to a desired system-related (target) operational state (for instance a blood flow of 300 ml/min) and determining a current/real value, which can be derived from the contamination of the dialysis liquid, for this system-related operational state, for which a shunt recirculation is assumed, determining an ideal value, which can be derived from the contamination of the dialysis liquid, for this system-related operational state, for which there is no recirculation in the ideal case, and defining the true shunt recirculation for this system-related operational state directly or indirectly from the current value and the ideal value.

The invention claimed is:

1. A control method for a blood purification system, comprising at least one blood inlet/outlet element and a blood purification apparatus to which the blood inlet/outlet element is connected or can be connected, the control method being adapted, for determining a recirculation during an extracorporeal treatment of the blood by means of the blood purification system and on the basis of the system response to an alteration of a system-related operating value, to carry out the following method steps:

determining a reference value, which can be derived from the contamination of a dialysis liquid, for a system-related operational state or a system-related operating value for which there is no recirculation or the recirculation is known in advance, operating the system at a desired system-related target operational state or at a desired system-related target operational value, being adapted for a treatment of a patient, and determining a current/real value, which can be derived from the contamination of the dialysis liquid, for the system-related target operational state or the system-related target operational value, determining an ideal value, which can be derived from the contamination of the dialysis liquid, for the system-related target operational state or the system-related target operational value, for which there is no recirculation in the ideal case, and calculating the true recirculation for the system-related target operational state or the system-related target operational value directly or indirectly from the current value and the ideal value.

2. A control method for a blood purification system according to claim 1 further comprising:

establishing, at the side of the purification liquid, a reference parameter which can be measured by sensor technology and represents the concentration of uremic toxins from the extracorporeal circulation for a predetermined system-related reference operating value at which there exists a state of completed purification without any recirculation, and calculating a target parameter for a system-related target operational value from the reference parameter;

presetting the system-related target operational value and establishing an actual parameter related to the system-related target operational value;

determining an actual comparative value from the actual parameter and the reference parameter or from the actual parameter and the target parameter related to the system-related target operational value, and establishing the absolute or relative difference between the actual comparative value and a system-specific target comparative value related to the system-related target operational value; and converting the differential value into a recirculation degree correlating thereto.

3. The control method according to claim 2, wherein the system-related operating value is a blood flow, a flow rate of a conveyor means, a rotational speed or a stroke of the conveyor means or a similar performance variable representing a volume flow, the characteristic parameter is an absorbance value or a similar optical or electromagnetic property value of uremic substances, and the comparative value is a clearance.

4. The control method according to claim 3, wherein the target clearance value, as the target comparative value, is a dialyzer-specific target clearance value previously established for the target blood flow as a system-related target operational value, at which a state with essentially no recirculation exists for the target blood flow.

5. The control method according to claim 3, wherein the difference between the target clearance value and the actual clearance value is calculated to provide the comparison result, the actual clearance value being calculated from the ratio between the measured actual absorbance value and the target absorbance value for the target blood flow calculated from the reference absorbance.

6. The control method according to claim 3, wherein the reference blood flow is selected to be 50 ml/min and the target blood flow is selected to be 300 ml/min.

7. The control method according to claim 3, wherein in instances when a calculated recirculation degree is unequal to 0%, a theoretical shunt flow is calculated from the known variables:
   a. target blood flow;
   b. ultrafiltration value; and
   c. recirculation degree.

8. The control method according to claim 3, wherein in cases when a recirculation degree amounts to 0%, a theoretical shunt flow can be determined by means of the following steps:
   a. establishing the actual clearance for an actual flow direction of the blood flow in the shunt;
   b. establishing a reference clearance with a flow direction which is inverse to the actual flow direction, of the same blood flow in the shunt; and
   c. determining the theoretical shunt flow from the product of the actual clearance and the reference clearance divided by the difference between the actual clearance and the reference clearance.

9. A control method for a blood purification system according to claim 1 further comprising:
   a. determining/measuring a reference parameter representing the contamination of the dialysis liquid, preferably the reference absorbance (A(50)), with a reference blood flow of preferably 50 ml/min and with the prerequisite that there is no recirculation;
   b. determining/measuring an actual parameter representing the contamination of the dialysis liquid, preferably the actual absorbance (A(BBF)), with the selected/desired target treatment flow (BBF), preferably at 300 ml/min as a system reaction;
   c. equating the measured reference parameter and a target parameter, preferably the theoretical target absorbance value (A(BBF,theo)), for an assumed, theoretical absence of recirculation for the selected treatment flow (BBF) as an identical value: A(50)=A(BBF,theo); and
   d. directly establishing the recirculation (Rec) from the ratio between the measured actual parameter, preferably the actual absorbance value (A(BBF)), and the target parameter, preferably the target absorbance value (A(BBF, theo)) corresponding to the reference absorbance value A(50), by means of the following:

$$Rec(\text{in \%}) = (1 - (A(BBF)/A(50))) * 100 \text{ or}$$

$$Rec(\text{in ml/min}) = (1 - (A(BBF)/A(50))) * BF.$$

* * * * *